United States Patent [19]

Fernandez et al.

[11] Patent Number: 4,994,019
[45] Date of Patent: Feb. 19, 1991

[54] MAGNETIC OCCLUDING DEVICE

[75] Inventors: Mario F. Fernandez, Los Olivos, Calif.; Loren R. Keldahl, Edina, Minn.; Dale C. Lindquist, Willmar, Minn.; Paul L. Miller, Minnetonka, Minn.

[73] Assignee: Micro-Magnetics, Inc., Willmar, Minn.

[21] Appl. No.: 474,680

[22] Filed: Feb. 6, 1990

Related U.S. Application Data

[63] Continuation of Ser. No. 387,398, Jul. 28, 1989, abandoned, which is a continuation of Ser. No. 149,405, Jan. 28, 1988, abandoned.

[51] Int. Cl.$^5$ .................................................. A61F 2/02
[52] U.S. Cl. ........................................ 600/30; 128/346; 128/DIG. 25; 251/5; 251/65; 600/31
[58] Field of Search .............................. 128/325–327, 128/346, 885, DIG. 25; 251/4, 5, 7, 9, 10, 65; 600/12, 29–32; 604/250

[56] References Cited

U.S. PATENT DOCUMENTS

| | | | |
|---|---|---|---|
| 3,419,008 | 12/1968 | Plishner | 128/346 |
| 3,476,355 | 11/1969 | Sherwood | 251/65 |
| 3,704,704 | 12/1972 | Gonzales | 128/1 R |
| 3,731,670 | 5/1973 | Loe | 128/1 R |
| 3,815,576 | 6/1974 | Balaban | 600/30 |
| 3,924,631 | 12/1975 | Mancusi, Jr. | 128/346 |
| 3,926,175 | 12/1975 | Allen et al. | 128/346 |
| 3,939,821 | 2/1976 | Roth | 128/1 R |
| 3,991,743 | 11/1976 | Bucalo | 128/1 R |
| 4,024,855 | 5/1977 | Bucalo | 128/1 R |
| 4,053,952 | 10/1977 | Goldstein | 3/1.1 |
| 4,154,226 | 5/1979 | Hennig et al. | 128/1 R |
| 4,360,007 | 11/1982 | Levy et al. | 128/1 R |
| 4,390,019 | 6/1983 | LeVeen et al. | 128/325 |
| 4,453,536 | 6/1984 | Abild | 600/30 |
| 4,496,133 | 1/1985 | Sule | 251/7 |
| 4,549,531 | 10/1985 | Trick | 128/1 R |
| 4,551,862 | 11/1985 | Haber | 623/14 |
| 4,552,128 | 11/1985 | Haber | 128/1 R |
| 4,556,050 | 12/1985 | Hodgson et al. | 128/1 R |
| 4,586,501 | 5/1986 | Claracq | 128/325 |

FOREIGN PATENT DOCUMENTS

| | | | |
|---|---|---|---|
| 2717607 | 10/1978 | Fed. Rep. of Germany . | |
| 3139811 | 4/1983 | Fed. Rep. of Germany . | |
| 2530947 | 2/1984 | France | 600/32 |
| 0224487 | 7/1985 | German Democratic Rep. | 128/325 |
| 1194358 | 6/1970 | United Kingdom | 128/DIG. 25 |

Primary Examiner—John D. Yasko
Assistant Examiner—Adam J. Cermak
Attorney, Agent, or Firm—Nickolas E. Westman

[57] ABSTRACT

A self-contained, implantable device for controlling passage of material through internal body conduits, and in particular to control the material passage through a closure point commonly referred to as a sphincter, such as flow through the urethra from the bladder, movement through the bowel, or flow of medications from an artificial conduit that is implanted. The magnetic occluding device comprises a fixed magnetic pressure plate assembly, positioned on one side of a conduit, and a permanent magnet on an opposite side of the conduit. The permanent magnet can be moved so that the magnetic force between the pressure plate and the magnet can be altered from a position wherein the attraction between the movable magnet and the pressure plate carries the conduit between the magnet and the pressure plate to collapse to close off flow through the conduit, to a position wherein the conduit can open. The position of the magnetic poles of the movable magnet is changed either by being rotated or displacing it laterally with the pressure plate so the magnets tend to at least slightly repel each other when the conduit is to be opened. Control of the magnetic force is achieved to insure that the flow of blood in the conduit is not cut off.

12 Claims, 3 Drawing Sheets

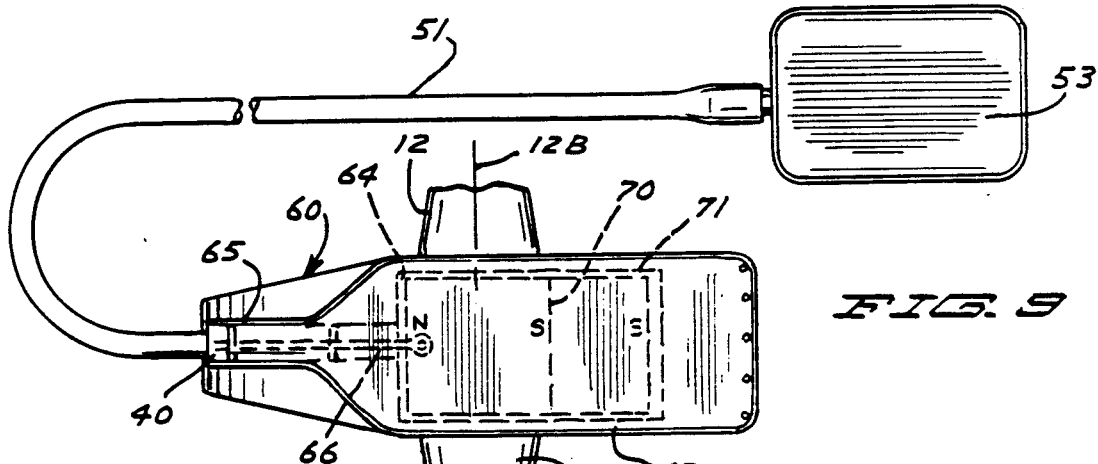
FIG. 9
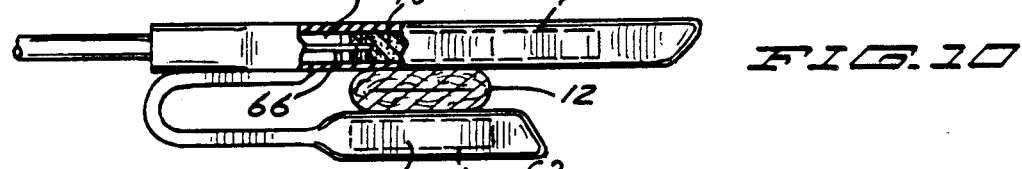
FIG. 10
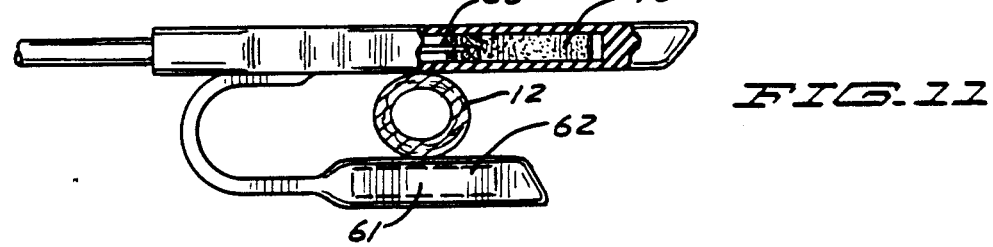
FIG. 11
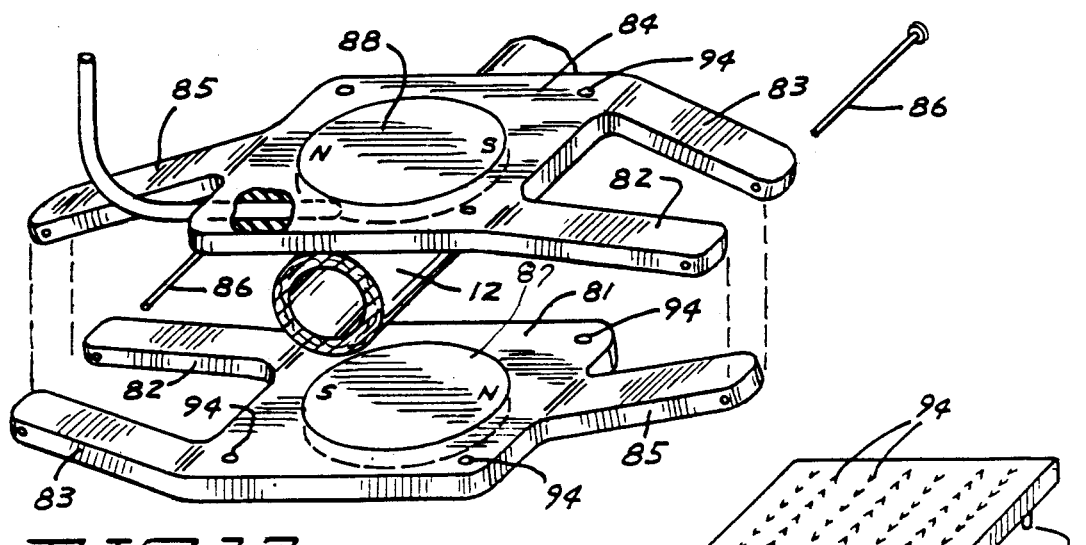
FIG. 12
FIG. 13

4,994,019

MAGNETIC OCCLUDING DEVICE

This is a continuation of application Ser. No. 07/387,398, filed July 28, 1989, now abandoned which in turn was a continuation of our application, Ser. No. 07/149,405, filed Jan. 28, 1988, now abandoned.

BACKGROUND OF THE INVENTION

1. Field of the Invention.

The present invention relates to a magnetically actuated device for controlling the flow of material through an internal bodily conduit at a closure point commonly called a sphincter.

2. Description of the Prior Art.

Artifical sphincters have been advanced in the prior art, and primarily the ones that are in use utilize an inflatable cuff surrounding a conduit to obturate material flow. In creating the localized pressure necessary to overcome the material back pressures, the cuff-type devices also will tend to obstruct the normal flow of blood in the conduit walls, and thus long term useage of cuff-type artificial sphincters is not viable. The continuous ring of pressure without adequate blood flow results in scarring and localized tissue damage.

A type of a magnetically actuated artificial sphincter is shown in United States Pat. No. 3,926,175 that shows a cuff having a platen section that is actuated by magnetic force to press against a conduit around which the cuff is placed. An external electromagnet is utilized for providing the force, and thus the device is not totally implantable, and is made so it will snap to a locked position and must be snapped back to an open position. While the device is made to apply forces only on two opposite sides of the conduit that it is surrounding, rather than in a noose-like complete ring in order to prevent necrosis, the unit is still difficult to operate, and varying the closing pressures is difficult because the magnet used is for actuation of an over center actuating device.

U.S. Pat. No. 4,024,855, issued May 24, 1977 to Bucalo describes a magnetic filament which may be implanted in the form of a pair of coils on opposite sides of a body tube such as a urethra. The coils both can be permanent magnet materials, or one can be a permanent magnet and the other a filament that has magnetic properties. The coils that are implanted are polarized so that they attract each other for the purposes of pinching the conduit or urethra closed. Then, in order to open the body conduit it is necessary to provide an external unit that creates a magnetic field which alters the polarity of the implanted coils so that the coils repel each other to open the tube. When drainage is over, the external power unit is used to return the implanted coils to their original polarity. It can be seen that such devices have limitations in the force that can be generated, and require the use of external controls for operation. Further, as a practical matter, controlling the pressure on the body conduit using these devices is difficult, so that leakage or dripping can occur, or the coils can cause closure which is too tight and then will cause damage to the tissue as well.

A magnetically actuated device for controlling a tube that carries fluid flow to or from different organs of the body of a human is shown in U.S. Pat. No. 4,053,952, but this uses a type of valve arrangement which has a coil with oppositely facing contact members on opposite sides of the tube. When current is supplied to demagnetize or magnetize permanent magnets installed, the tube can selectively be blocked or opened. An external current of substantial value is required in order to operate the unit, and while it is indicated that power consumption is low, there still is a need for external power. The device shown in Patent '952 can be used as a pump as well, in one form of the invention by alternately magnetizing and demagnetizing provided permanent magnets.

Magnetically controlled plugs have been advanced for controlling incontinence, and such devices are shown in West German Patents DE2717607 and DE 3139811. Other similar plug devices are known, but they do not use magnetic forces for collapsing or closing off an internal bodily conduit.

SUMMARY OF THE INVENTION

The present invention relates to a magnetic occluding device for an internal body conduit or tube that carries material through the conduit, such as the urethra that carries flow from the bladder, or a conduit such as the bowel. The device essentially acts as an artificial sphincter that is controllable in force, reliable in operation, and is easily totally implanted. In a preferred form shown, actuation means comprises a pressure transducer that can be operated manually, with a finger or digit, to provide a force for actuation.

The occluding device comprises a pressure plate positioned on one side of a body conduit. The pressure plate is a flat permanent magnet that has magnetic poles on opposite sides or ends of the pressure plate, and a control magnet is positioned on an opposite side of the body conduit from the pressure plate. The pressure plate and the control magnet in the preferred form each have poles that are adjacent the lateral edges of the conduit, so that in one position the poles of the two magnets that are of opposite polarity are substantially aligned, creating a magnetic force that tends to draw the magnets together and collapse the conduit or tube with which the occluding device is used, to close off flow through the tube. The pressure plate and the actuating magnet are mounted in housings that are suitable material such as Silastic brand silicon-based plastic, or other plastic or synthetic materials that are compatible with the human body, and which can be sutured in place or otherwise held in position. The surfaces of the occluding device that contact the conduit are made so that they will have irregular surface shape, such as small lugs or surface grooves, that will permit blood flow in the conduit tissue, while closing off material flow through the interior passageway of the conduit. The conduit contact surfaces are biologically adapted for permitting blood flow.

The actuation of the actuating magnet is accomplished in the preferred form of the invention through the use of a hydraulic actuator that has a piston and piston rod. The piston rod controls movement of the actuating magnet to move it so that the poles of the actuating magnet move out of registry with the pressure plate magnet to a point where the magnetic forces are at least substantially balanced, if not repelling, so that the body conduit can expand. When the actuating magnet is moved to a position where the same polarity magnetic poles of the pressure plate and the actuator magnet are influencing each other they tend to repel and urge the magnets apart to open the conduit they control.

In a second form of the invention, the actuating magnet can be slid laterally of the conduit to a position wherein one of the poles of the actuating magnet is laterally spaced from the conduit, while the other pole is in registry with a similar pole on the pressure plate to provide a repelling force that moves the pressure plate and the actuating magnet apart.

Various types of supporting structures can be utilized for holding the magnetic devices in proper location. The pressure plate and the housing for the actuating magnet can be sutured to adjacent tissue for insuring that the magnets will not shift in an unwanted manner during actuation. The force of attraction of the magnets can be controlled by regulating the magnet size and to a certain extent by changing the spacing of the magnets when the conduit is fully collapsed by adjusting the thicknesses of the supporting material between the magnets as illustrated in a third form of the invention. This insures that excessive compressive forces will not be applied, so that blood flow is maintained. The pressure plate magnet and the actuating magnet do not encircle the conduit. Thus, blood flow is permitted along the edges of the conduit, which is different from the pneumatic or hydraulic cuff-type sphincters.

The present device is relatively low-cost to manufacture, and can be made with existing materials. It also is reliable, and while the actuation in the form shown is completely within the body, different actuators can be utilized for external force provisions for shifting the actuating magnet to a position to permit the conduit to open.

Further, the pressure plate could be made of magnetic materials along the edges of the conduit and nonmagnetic materials in the center, so the closing force of the actuating magnet would reduce when the poles of the actuating magnet are rotated to overlie the nonmagnetic portions of the pressure plate.

BRIEF DESCRIPTION OF THE DRAWINGS

FIG. 9 is a top view of a modified form of the invention in a view similar to that shown in FIG. 2;

FIG. 10 is an end view of the device of FIG. 9 in a position with the conduit closed or occluded;

FIG. 11 is a view similar to FIG. 10 showing the conduit in an open position;

FIG. 12 is an exploded perspective view of a further modified form of the invention utilizing a different type of magnet mounting device; and FIG. 13 is a perspective view of a pad that may be used with the mounting device of FIG. 12 for providing different spacings between a pressure plate and actuating magnet.

DETAILED DESCRIPTION OF THE PREFERRED EMBODIMENTS

Figure 1:
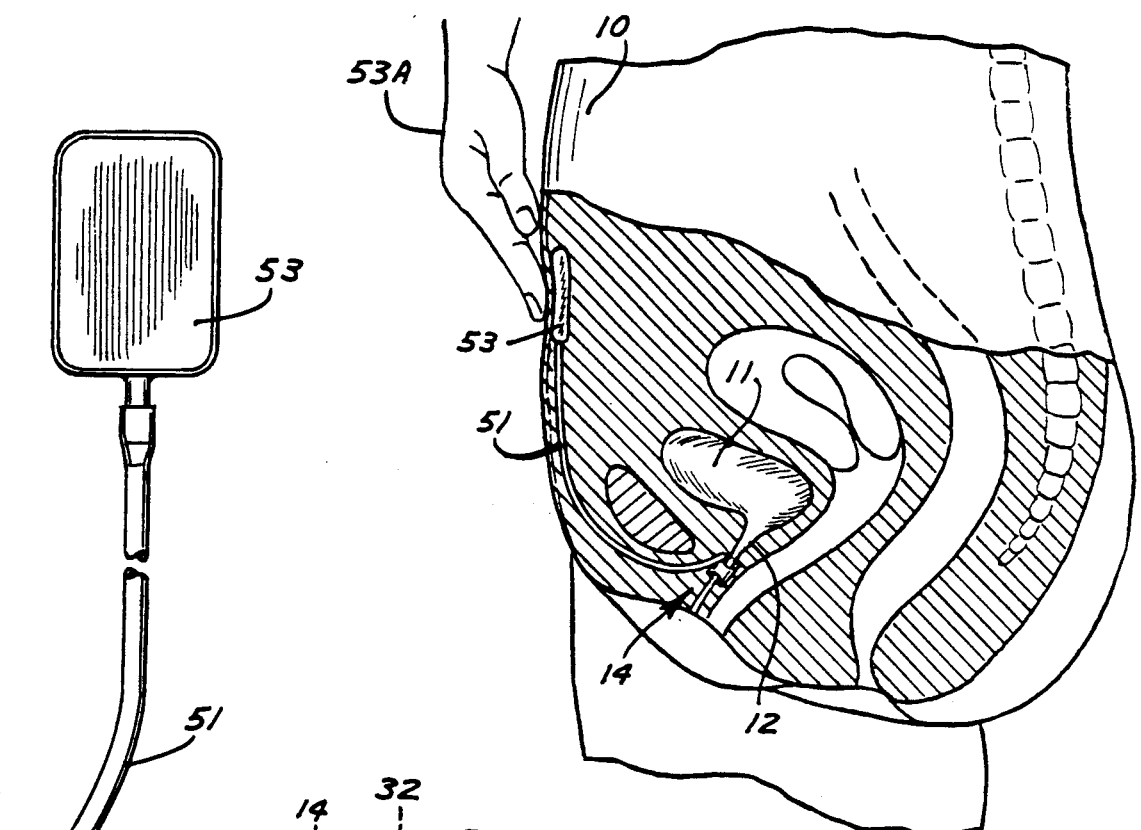
FIG. 1 is a sectional view of a portion of a body of a human showing the device of the present invention implanted for controlling flow through the urethra.

In FIG. 1, a human body indicated generally at 10 is illustrated schematically. A bladder 11 is illustrated along with a urethra 12 leading from the bladder. When incontinence occurs, the sphincter for the urethra becomes uncontrollable for one reason or another, and to correct the problem in accordance with the present invention, a magnetic occluding device indicated generally at 14 is provided for implantation in the human body in association with the urethra or conduit 12, for providing manual actuation on a totally implanted occluding device. The magnetic occluding device is shown in more detail in the first form of the invention in FIGS. 2 through 8, and includes a mounting assembly 15, that can be of various configurations, but includes a pressure plate housing 16 on one side of the conduit or urethra 12, and an actuating magnet housing 17 on an opposite side thereof. The housings comprise an outer covering of Silastic or plastic material indicated generally at 20 and 21, respectively, which have surfaces 20A and 21A that face the conduit or urethra 12. The surfaces are provided with irregularities, as shown, that are for insuring that there will be adequate blood flow through the urethra 12 (or other body conduit) by permitting intermittent contact with the outer tissue of the urethra 12.

The housings 16 and 17 are joined with a connector 23 that is to one side of the urethra 12, and can be used for positioning the housings. The connector 23 can have suitable openings therein for suturing it in place, as can the housings 16 and 17 as shown by sutures 27.

The pressure plate housing 16 has a pressure plate permanent magnet 28 installed therein, and this can be covered with a separate layer of material if desired or directly embedded in the outer material 20. The pressure plate magnet 28 includes north and south poles as designated by N and S in the figures, for example in FIGS. 3 and 4. While the pressure plate magnet 28 is shown as a disc, the magnets can be bar magnets if desired of rectilinear form, or other desired shapes.

The housing 17 has a actuating magnet assembly 30 mounted and embedded within the embedding material 21 (FIGS. 5-8), and positioned so that it is aligned with the pressure plate magnet 28. The assembly 30 includes an outer case 31 that is circular in cross-section, in which the actuating magnet 32 is mounted in this form of the invention. The case 31 can be molded from plastic or made of other suitable materials. The actuating magnet 32 is a permanent magnet in this form, but formed with the north and south poles on opposite ends of a diametral line, much like a bar magnet. Such a diametral line, which will be referred to as a reference axis or line, is shown at 32A in the drawings.

The casing 31 has an integral sleeve 34 formed therein, which is tubular, and has an interior passageway 34A. The sleeve 34 extends outwardly from the embedding material, so that it has an outwardly extending neck portion 35, as can be seen in several of the figures, and this neck portion includes a coupling bellows or sleeve 37 that couples a hydraulic or fluid pressure actuator 40 to the sleeve, and in alignment therewith. The actuator 40 comprises an outer cylindrical housing 41, and an interior piston 42 that has a piston rod 43 that is sealingly slidably mounted relative to the cylindrical housing 41, and extends into the passageway 33 of the sleeve. An actuator rod 44 has a head member 45 that is slidably mounted in the passageway 33, and which has an outer actuating "T"-head 46 that is positioned in a cross hole and horizontal slot indicated generally at 47 of a plastic insert 48. The insert 48 has a slot 48A (FIG. B) opening to the hole for the "T"-head 46 to permit receiving the "T"-head 46 when the rod 43 is positioned all the way to one edge of the slot 47 so the "T"-head can be inserted in a known manner. The magnet has a pie-shaped recess 49 to receiving insert 48 and when the insert 48 is in place in casing 31, the rod 44 and head 46 will be securely retained.

A cover plate 50 used to enclose casing 31 on the top and it can be cemented or sonic welded in place to hermetically seal the case interior. This will trap the insert 48 in place so it will not fall out.

The cylindrical housing 41 of the actuator 40 has an outer end connected to a conduit 51 that in turn is connected to a flexible wall reservoir 53 of suitable size which contains a non-toxic liquid that will provide sufficient volume for actuation of the fluid pressure actuator 40.

As can be seen in FIG. 1, the reservoir 53 is subcutaneously implanted in the abdomen area, and the conduit 51 can also be run subcutaneously down to the magnetic occluding device 14.

Figure 2:
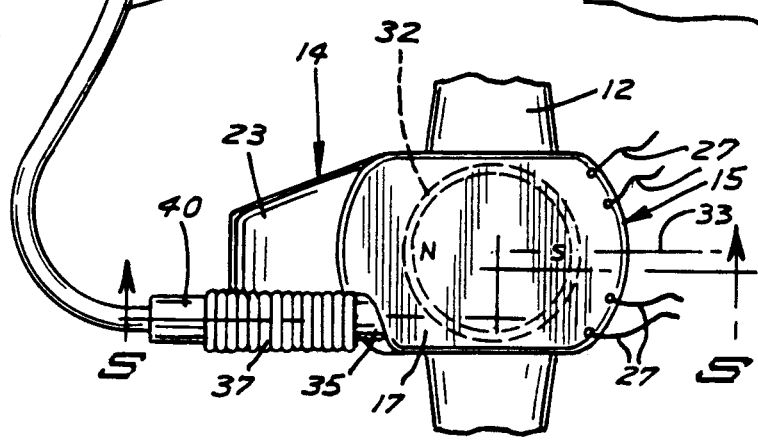
FIG. 2 is a schematic representation of a first form of the device of the present invention shown installed on a bodily conduit.
Figure 3:
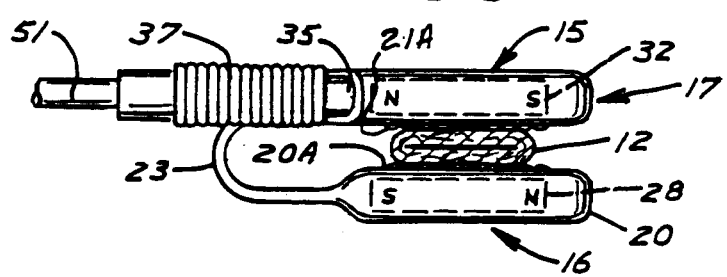
FIG. 3 is an end view of the device of FIG. 2 with the conduit shown collapsed for closing.
Figure 4:
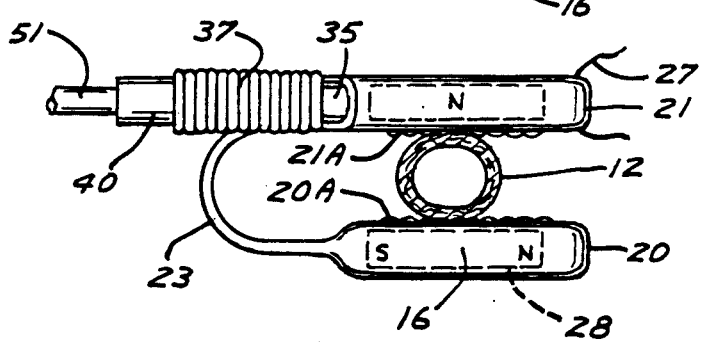
FIG. 4 is a sectional view similar to FIG. 3 showing the conduit in its open position.
Figure 5:
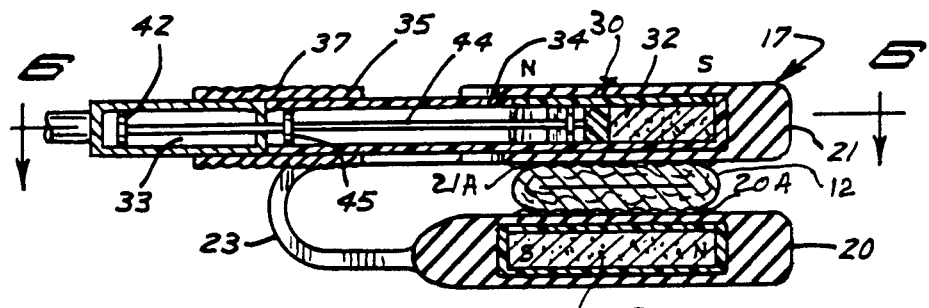
FIG. 5 is a sectional view taken as on line 5—5 in FIG. 2.
Figure 6:
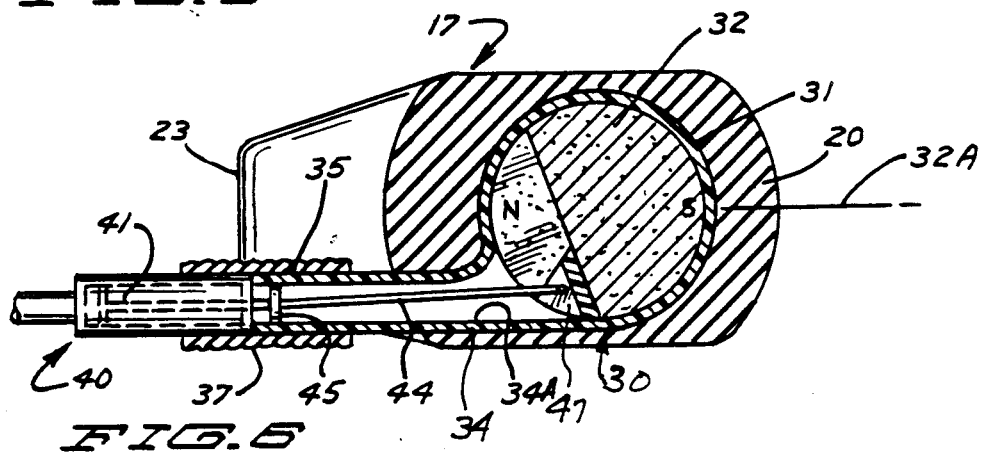
FIG. 6 is a sectional view taken as on line 6—6 in FIG. 5.
Figure 7:
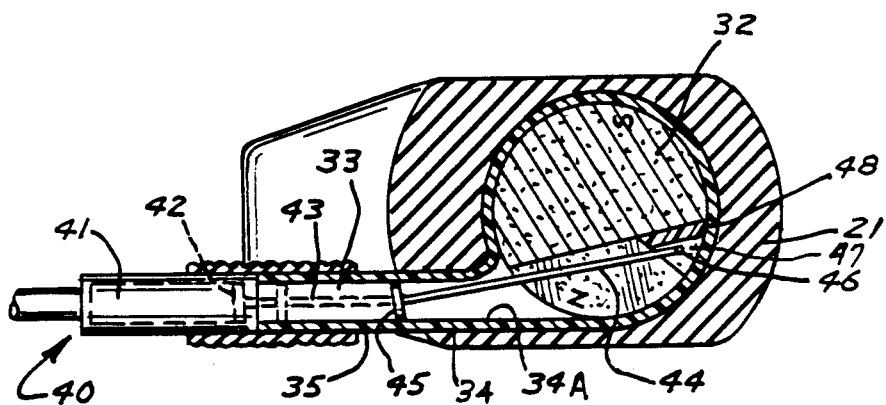
FIG. 7 is a sectional view showing the device in the process of being actuated.
Figure 8:
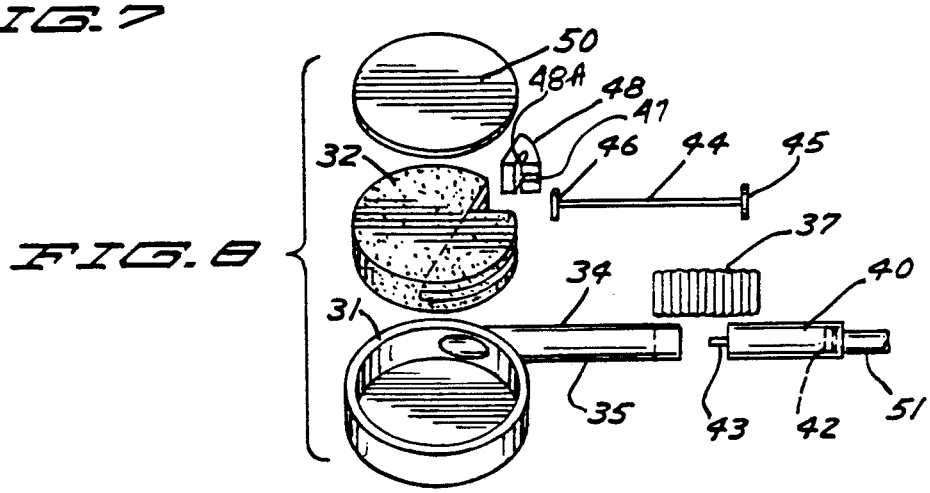
FIG. 8 is an exploded view of the actuating elements of the device of FIG. 7.

In its normal position, without any external pressure on the flexible wall reservoir 53, the piston 42 is at an outer end of the cylindrical member 41 of the actuator, and the actuating rod 44 is retracted to a position shown in FIG. 6 for example, as well as in FIGS. 2 and 3. In this condition, the south magnetic pole of actuating magnet 32 is substantially directly aligned across the urethra with the north magnetic pole of the pressure plate magnet 28, and the north magnetic pole of the actuating magnet is substantially directly aligned on the opposite side of the conduit or urethra 12 with the south magnetic pole of the pressure plate magnet 28. The magnetic force is at a maximum, thereby collapsing the conduit or urethra 12 as shown in FIGS. 3 and 5 for example, so that flow through the conduit 12 is not permitted. Again, the surface configurations shown at 20A and 21A are such that the blood flow will be permitted through the tissue area of the urethra or conduit 12, but as the bladder fills, the magnetic force will insure that the urine is not permitted to pass through the urethra until the device is actuated by the patient.

When the bladder is to be relieved, the reservoir 53 can be pressed with a finger from the exterior of the abdomen, through the skin, to collapse the wall of the reservoir to force liquid through the conduit 40 against the piston 42, to in turn cause the end of rod 43 to bear against guide 45 and force the rod 44 to extend out through the passageway 33 and turn or pivot the actuator magnet 32. The south pole of the actuator magnet 32 is moved to a position wherein it is closer to the south pole of the pressure plate magnet than it is to the north pole (to get repulsion) or vice versa, that is so the north pole of the actuator magnet is closer to the south pole of the pressure plate. A repelling force urges the magnet, and their supporting housings apart to permit the urethra 12 to expand and provide a passageway for emptying the bladder.

When the bladder is empty, the pressure on the reservoir 53 can be relieved, and the repelling magnetic forces between the pressure plate magnet and the actuator magnet will cause the actuator magnet 32 to start to rotate in its casing 31 back to its initial position, and the attractive forces will cause the magnets to return to registry and at the same time force the liquid back into the reservoir 53. The piston 42 will thus move to its initial position and the magnets will again clamp the urethra or conduit 12 closed.

A suitable lubricant can be contained in the casing 31, so that the magnet 32 slides easily, and little effort is required for movement. The force from the pressure of a finger or digit on the reservoir 53 is adequate to insure that the actuating magnet 32 will be moved so that its polarity causes repulsion or at least a sufficient release of force so that the pressure from the bladder will insure that the urine can pass through the urethra.

The same type of action can be used with other bodily conduits, such as for bowel control, or control of medication from a supply that is implanted with an implanted conduit leading to an organ.

Other types of actuators for the magnet can be utilized other than a fluid cylinder and reservoir, such as an external magnetic field that would collapse the reservoir, or an external magnetic field that would act directly on an actuator to move or rotate the actuating magnet 32 of the occluding device.

In FIGS. 9, 10 and 11, a modified form of the invention is shown. Instead of having a housing or casing that is cylindrical, the magnetic occluding device 60 that is shown therein has a rectangular pressure plate assembly 61 that is similar in construction to the pressure plate housing 16, and includes a pressure plate magnet 62 embedded in a suitable material. In this form, both of the magnets are rectangular with the north and south poles aligned for causing occlusion as previously described.

In this form of the invention, an upper housing 63 has a case 64 embedded therein. The case 64 has a neck 65, and an actuating rod 66 that corresponds generally to the actuating rod 44. The neck 65 has the conduit 51 connected thereto. The actuator 40 is thus also connected to conduit 51 leading from a reservoir 53 which is the same as in the first form of the invention.

Actuation of the reservoir 53 in this form of the invention, however, will cause an actuating magnet shown at 70 to slide transversely of the longitudinal axis shown at 12B of the urethra or conduit 12, to a position as shown generally in dotted lines at 71, so that the north pole of the actuating magnet 70 will be generally aligned with the north pole of the pressure plate magnet 62. The magnetic attraction will no longer be sufficient to hold the urethra closed and in fact, repulsion will cause the pressure plate and actuating magnets to move apart so the urethra 12 will open as shown in FIG. 11.

The outer casing 64 also could merely have tracks or rails that are of low friction material for slidably mounting the magnet 70. Suitable lubricants can be used to insure that the magnet 70, which is the actuating magnet, will move to a position to reduce the magnetic force between the actuating magnet and the pressure plate magnet so that release of closing pressure on the conduit or urethra 12 can be accomplished.

Here too, the repelling force between north and south poles or the reduction in magnetic attraction force will be sufficient so the urethra will open. When the reservoir is released, the repulsion force will start the actuating magnet to move to its home position, and then the attraction force between the opposing poles will cause a closing of the conduit when the two magnets come back into registry.

In FIGS. 12 and 13, a modified magnet and pressure plate supporting device is shown, which can be used with either of the forms of the actuating magnets illustrated. However, in this form it is illustrated with the rotational actuating magnet, and comprises a first support member 80 and a second support member 81, which are identical but inverted and reversed. Each of the support members 80 and 81 has a pair of legs 82 and 83 that are positioned on one end of a central plate member 84, and which are spaced apart at their outer ends to receive a single leg 85 that is at the opposite side of the central plate member 84 of the other support member. A suitable non-toxic material pin 86 can be inserted through provided apertures in the ends of the arms 82 and 83, and through an aperture in the single arm 85 (when it is properly aligned) and hold the unit in assembly with the urethra or body conduit 12 passing through the assembly between plates 84.

The magnetic pressure plate member is shown at 87 on one of the central plate members 84, and the actuator magnet 88 is shown on the other. The actuator magnet 88 is formed exactly as previously explained in relation to FIGS. 1 through 5. The pressure plate magnet can be the same as the actuator magnet with the actuator removed.

In this form of the invention, a pressure pad insert 92 is made in several different thicknesses, and each pad 92 includes locator pegs 93 that will fit into apertures 94 on the central plate members 84. The pressure pads 92 can then be used to change the distances that the respective pressure plate magnet 87 and the actuator magnet 88 are spaced apart when the urethra 12 is collapsed. The surface of the pads 92, which contact the urethra as shown, can have surface configurations indicated at 94 to provide a biological surface that permits flow of blood in the urethra.

The magnet strength can be varied so that desired pressures can be obtained, but with the form of the invention shown in FIGS. 12 and 13, the spacing between the magnets is controlled and selected by the surgeon that is implanting the occluding unit, to provide for different forces using the same strength magnets merely by increasing the spacing of the magnets. The thickness of pads 92 changes the magnet spacing when the conduit that is being controlled has collapsed.

The actuator magnet can be operated as previously explained, so that the conduit can be closed off or opened as desired. The pads 92 also can have suitable interlocks or guides on opposite sides that mate with complementary guide members on the aligning pad to provide means to hold the pads in registry. The members 80 and 81 can be sutured in place if desired.

The magnets that are shown have sufficient length along their axes 36 so that the poles and the force thereof are across a substantial lateral width of the conduit, that is, they are sufficient so that they will span the width of the conduit and provide magnetic forces to clamp the conduit and hold the conduit or urethra between the actuating magnet and the pressure plate magnets securely.

Sensors that monitor bodily functions can be used for controlling the actuator. For example, blood pressure sensors for arterial pressure can provide an actuator signal, or actually blood can be diverted to operate the actuator directly. Lung pressure also could be used for the fluid pressure actuator.

If desired, the actuator could be locked open by using a check valve in the conduit 51 which could be released upon an independent signal to permit the actuator to return to position with the conduit closed.

Although the present invention has been described with reference to preferred embodiments, workers skilled in the art will recognize that changes may be made in form and detail without departing from the spirit and scope of the invention.

What is claimed is:

1. A magnetic occluding device for a conduit in a body comprising:
   first and second assembles, said assemblies including means for mounting the assemblies on opposite sides of a bodily conduit;
   at least a first of said assemblies including magnet means having a pair of poles that are spaced apart in a reference direction passing through the poles, said magnet means being movably mounted on the first assembly for movement between first and second positions, the reference direction of the poles being substantially transverse to the conduit in one of said positions;
   a second of said assemblies including means that are magnetically attracted to the poles of the magnet means in a first position of the magnet means the magnet attraction between the two assemblies is substantially reduced to permit a bodily conduit placed between the assemblies to expand, the magnet means being movable between the first and second positions in a direction parallel to a plane defined by the second assembly; and
   means for actuating the magnet means between the first and second positions.

2. The apparatus as specified in claim 1 wherein the means for actuating comprises a fluid pressure actuator coupled to the magnet means, and a reservoir for containing fluid fluidly connected to the actuator and which can be subjected to pressure to move the actuator, whereby upon pressure being applied to said reservoir, the magnet means is moved to its second position.

3. The apparatus as specified in claim 2 wherein both of said assemblies include permanent magnet means, and at least one of said magnet means being movable.

4. A magnetic occluding device according to claim 1 wherein said magnet means is rotatably mounted on one of the first and second assemblies for actuation about a rotational axis, the magnetic poles being movable substantially 90° about the rotational axis of the magnet means to vary the magnetic attraction between the two assemblies.

5. A magnetic occluding device for a bodily conduit comprising a totally implantable member having first and second housings;
   means for supporting said first and second housings on opposite sides of a bodily conduit, said first housing having first magnet means therein;
   means forming a part of the second housing to provide for attraction of the first magnet means toward the second housing, said means to provide attraction having regions of greater and less magnetically attractive capabilities for the first magnet means, whereby in the first position of the first magnet means the conduit between the assemblies is collapsed to be closed, and in the second position of said first magnet means, the magnetic force reduces sufficiently to permit the conduit to open; and
   means for moving the first magnet means between its first and second postions.

6. The apparatus as specified in claim 5 wherein said first magnet means is rotatably mounted with respect to the second housing to shift the position of the magnetic poles thereon to control the magnetic force with respect to the second housing.

7. The apparatus as specified in claim 5 wherein said first magnet means is movable laterally with respect to a longitudinal axis of the conduit with which the housings are associated, wherein the magnetic poles of the first magnet means are changed in position upon laterally linear sliding movement.

8. The apparatus as specified in claim 5 wherein the second of the housings includes a second magnet means, the second magnet comprising the means for providing attraction for the first magnet, the first and second magnet means having poles that are generally aligned across the conduit in a first position of the first magnet means, and wherein the magnetic poles of the first and second magnets are offset sufficiently to reduce the magnetic force with the first magnet means in its second position.

9. The apparatus of claim 8 wherein the housings are implantable in the body, and actuator means for moving the first magnet means between its respective positions, said actuator means being totally implantable in a body and having means manually operable from the exterior of the body for moving the first magnet means to its second position.

10. The apparatus of claim 9 wherein the first magnet means is rotatably mounted with respect to the second housing.

11. A magnetic occluding device for a bodily conduit comprising a totally implantable member having first and second housings;

- means for supporting said first and second housings on opposite sides of a bodily conduit, the first housing having first magnet means therein;
- means forming a part of the second housing to provide for attraction of the first magnet means toward the second housing, said means to provide attraction having regions of greater and less magnetically attractive capabilities for the first magnet means, whereby in a first position of the first magnet means the conduit between the assemblies is collapsed to be closed, and in a second position of said first magnet means, the magnetic force reduces sufficiently to permit the conduit to open;
- said housings comprising interchangeable substantially identical housing members that are reversed and inverted when placed on opposite sides of the conduit, each of said housing members each having a central pad and a pair of spaced apart legs on one end of the pad, and a single leg on an opposite side of the pad, the single leg of each housing member interfitting between the pair of legs from the other housing member, the interfitting legs being oriented on each of opposite lateral sides of the conduit when placed on a conduit; and
- pin means for holding the respective interfitting single legs and the associated pair of legs together whereby the legs can permit the housing members to span the conduit on which they are placed and to be able to move apart, the first magnet means and the means for providing attraction being mounted on the pads of the respective first and second housing members and being aligned with the conduit on opposite sides thereof when the housing members are placed on a conduit.

12. The apparatus as specified in claim 11 and means for spacing the magnet means of the housing members a different distance apart when the conduit is collapsed, comprising removable spacer means for positioning between the housing pads and the conduit to vary the spacings of the magnet means.

* * * * *